United States Patent [19]

Duclos et al.

[11] Patent Number: 5,818,577
[45] Date of Patent: Oct. 6, 1998

[54] DETECTION METHOD AND APPARATUS FOR CONTAMINATION IN QUARTZ SAND

[75] Inventors: Steven Jude Duclos, Clifton Park; Alok Mani Srivastava, Schenectady; Jacob Charles Borscheller, Clifton Park; Russell Stephen DeMuth, Berne; Victor Lien Kong Lou, Niskayuna, all of N.Y.

[73] Assignee: General Electric Company, Schenectady, N.Y.

[21] Appl. No.: 775,379

[22] Filed: Dec. 30, 1996

[51] Int. Cl.⁶ .......................... G01N 21/28; G01N 21/85; G01N 21/64

[52] U.S. Cl. ..................... 356/237; 356/38; 250/461.1; 250/458.1

[58] Field of Search ............................... 356/237, 335, 356/336, 338, 339, 445, 317, 318, 30, 38; 250/46.1, 458.1, 461.2, 563, 572

[56] References Cited

U.S. PATENT DOCUMENTS

| | | | |
|---|---|---|---|
| 3,598,994 | 8/1971 | Markle | 356/317 |
| 4,377,340 | 3/1983 | Green et al. | 356/237 |
| 4,723,659 | 2/1988 | Billion | 356/237 |
| 4,976,540 | 12/1990 | Kitamura et al. | 356/237 |
| 5,118,181 | 6/1992 | Yifrach et al. | 356/30 |
| 5,206,699 | 4/1993 | Stewart et al. | 356/30 |
| 5,414,520 | 5/1995 | Joss et al. | 356/238 |

OTHER PUBLICATIONS

N.R.J. Poolton et al., "On the Relationship Between Luminescence Excitation Spectra and Feldspar Mineralogy," Radiation Measurements, vol. 26, No. 1, pp. 93–101, (1996).

*Primary Examiner*—Hoa Q. Pham
*Attorney, Agent, or Firm*—Ernst G. Cusick; Noreen C. Johnson

[57] ABSTRACT

A method and apparatus for detecting impurities in quartz sand. The apparatus comprises at least one light source; at least one light detector assembly; a transport device; and a signal processor that receives the at least one signal from the at least one light detector assembly. The method comprises moving the quartz sand; illuminating the quartz sand to excite luminescence emission from impurities; receiving luminescence emission from the impurity; generating at least one signal indicative of the excited luminescence emission from the impurity; and determining if the signal represents an impurity in quartz sand.

36 Claims, 8 Drawing Sheets

DETECTION METHOD AND APPARATUS FOR CONTAMINATION IN QUARTZ SAND

BACKGROUND OF THE INVENTION

1. Field of the Invention

The invention is directed to detection method and apparatus for contaminants or impurities in sand, particularly quartz sand. The detection method and apparatus can detect contaminants in the sand, their amount, and can reduce the contaminants, if desired.

2. Background of the Invention

Quartz sand is used to make many different devices, including crucibles to melt and hold liquefied silicon. However, the quartz sand inherently contains impurities, such as but not limited to, Feldspar; alkalis including sodium (Na), lithium (Li), potassium (K), rubidium (Rb), cesium (Cs) and/or francium (Fr); iron (Fe); aluminum (Al); inorganic and organic matter and other such compositions. These are undesirable in many applications in which quartz sand is used, especially as a quartz melt. The impurities adversely effect many properties of the quartz, including the optical and electrical properties, as well as the properties of materials synthesized in contaminated quartz crucibles.

For example, in crucibles fabricated from melted quartz, deleterious warts are often formed throughout the crucible and on both interior and exterior surfaces of the crucibles. While the exterior surface of the crucible does not contact silicon in the crucible, interior surface warts, which are formed from the impurities in the quartz sand, often lead to contamination in the silicon melt. Thus, the impurities that form the warts are undesirable in the quartz melt and/or articles formed from melted quartz.

It is advantageous to minimize and/or remove the impurities in the quartz sand raw material prior to the quartz sand being used to make an article. This provides a reduced impurity quartz sand.

Contamination in quartz has been linked to Feldspar contamination in the starting quartz sand raw material. The elimination of warts, such as Feldspar warts, in quartz crucibles requires the detection and reduction of Feldspar impurities from the starting quartz sand raw material.

SUMMARY OF THE INVENTION

Accordingly, it is one object of the invention to provide a method and apparatus for the detection of impurities in quartz sand that overcomes the above-noted disadvantages.

It is an object of the invention to provide a method for detecting and/or reducing the impurities in sand, in particular quartz sand.

It is still another object of the invention to provide an apparatus for detecting and/or reducing the impurities in sand, in particular quartz sand.

This invention is directed to a method and apparatus for the accurate detection of impurities or contamination in sand. The sand may be quartz sand that is melted to form articles. These articles can then be used in holding and containing silicon melt for the formation of articles from molten silicon.

It is a further object of the invention to provide a method and apparatus for the detection of impurities or contamination, such as Feldspar, in quartz sand lots, for example, by using a red luminescence emission of $Fe^{3+}$ that is present as an impurity in Feldspar.

These and other objects, advantages and salient features of the invention will become apparent from the following detailed description, which, when taken in conjunction with the annexed drawings, discloses preferred embodiments of the invention.

BRIEF DESCRIPTION OF THE DRAWINGS

While the novel features of this invention are set forth in the following description, the invention will now be described from the following detailed description of the invention taken in conjunction with the drawings, in which:

FIGS. 7A–7C are examples of subsets of data within a region of interest;

DETAILED DESCRIPTION OF THE DRAWINGS

Quartz sand is used in the manufacture of many different articles, including, but not limited to, crucibles for melting and holding liquefied materials, such as melted silicon. However, the quartz sand, which is used to make these articles, inherently contains many impurities. These impurities include, but are not limited to Feldspar; alkalis, such as sodium (Na), lithium (Li), potassium (K), rubidium (Rb), cesium (Cs) and/or francium (Fr); iron (Fe); aluminum (Al); inorganic and organic matters and other such compositions. These impurities are undesirable in many quartz applications because they remain in the quartz melt, and adversely effect properties of the silica in the quartz sand.

In particular, impurities or contamination in quartz articles made from quartz sand has been linked to Feldspar contamination in the starting quartz sand material. While the following description discusses Feldspar as an impurity in the quartz sand, this is for ease of the description only. It should be readily understood by those skilled in the art that the scope of the invention includes any luminescent or optically detectable impurity, such as those discussed above and others, are interchangeable with the Feldspar in the following description.

To achieve essentially impurity free quartz article, it is desirable to detect and/or reduce the impurity from the quartz, both the quartz used as a raw quartz sand material and the quartz melt. Here, for example, the elimination of Feldspar in quartz sand requires the detection and reduction of the Feldspar impurities from the starting sand lots, i.e. quartz sand raw material.

One method, in accordance with the invention, detects the Feldspar (or as discussed above any other impurity) by exciting a Feldspar impurity with an appropriate energy source. For example, it has been determined that detection of Feldspar can be seen based on a generally red luminescence of $Fe^{3+}$ ions, which are naturally present in Feldspar. These $Fe^{3+}$ ions are tetrahedrally coordinated $Fe^{3+}$ ions, and are excited when an appropriate light source is illuminated on the quartz sand to produce the generally red luminescence.

Figure 1:
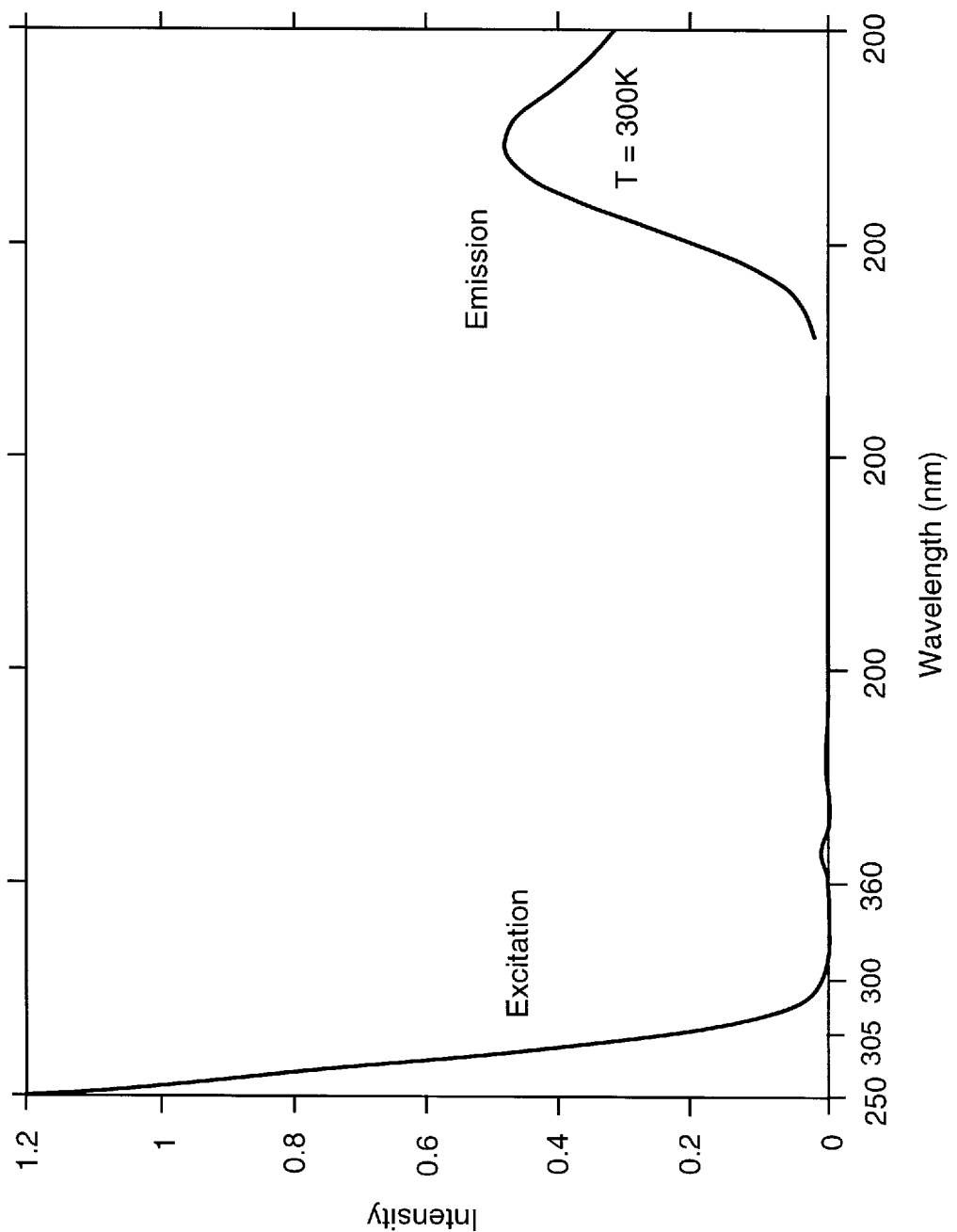
FIG. 1 is an excitation spectrum of the $Fe^{3+}$ emission ($\lambda_{em}$ equals about 750 nm) at T equals about 300 K.

FIG. 1 illustrates the excitation spectrum of the $Fe^{3+}$ emission with $\lambda_{em}$ equal to about 750 nm at a temperature T equal about 300 K for Feldspar. As illustrated in FIG. 1, a strong broad excitation band with a maximum at about approximately 260 nm in the Feldspar excitation spectrum is assigned to an $O^{2-} \rightarrow Fe^{3+}$ charge transfer transition. A diffuse reflectance spectrum, also illustrated in FIG. 1, is in agreement with the determined excitation spectrum.

The corresponding emission spectrum for a charge transfer excitation at $\lambda_{em}$ equals about 680–850 nm exhibits a broad band centered at approximately 750 nm, as illustrated in FIG. 1. This charge transfer excitation emission at $\lambda_{ex}$ equals about 260 nm is attributed to a $^4T_1(G) \rightarrow ^6A_1$ transition of the $Fe^{3+}$ ion in the Feldspar.

Figure 2:
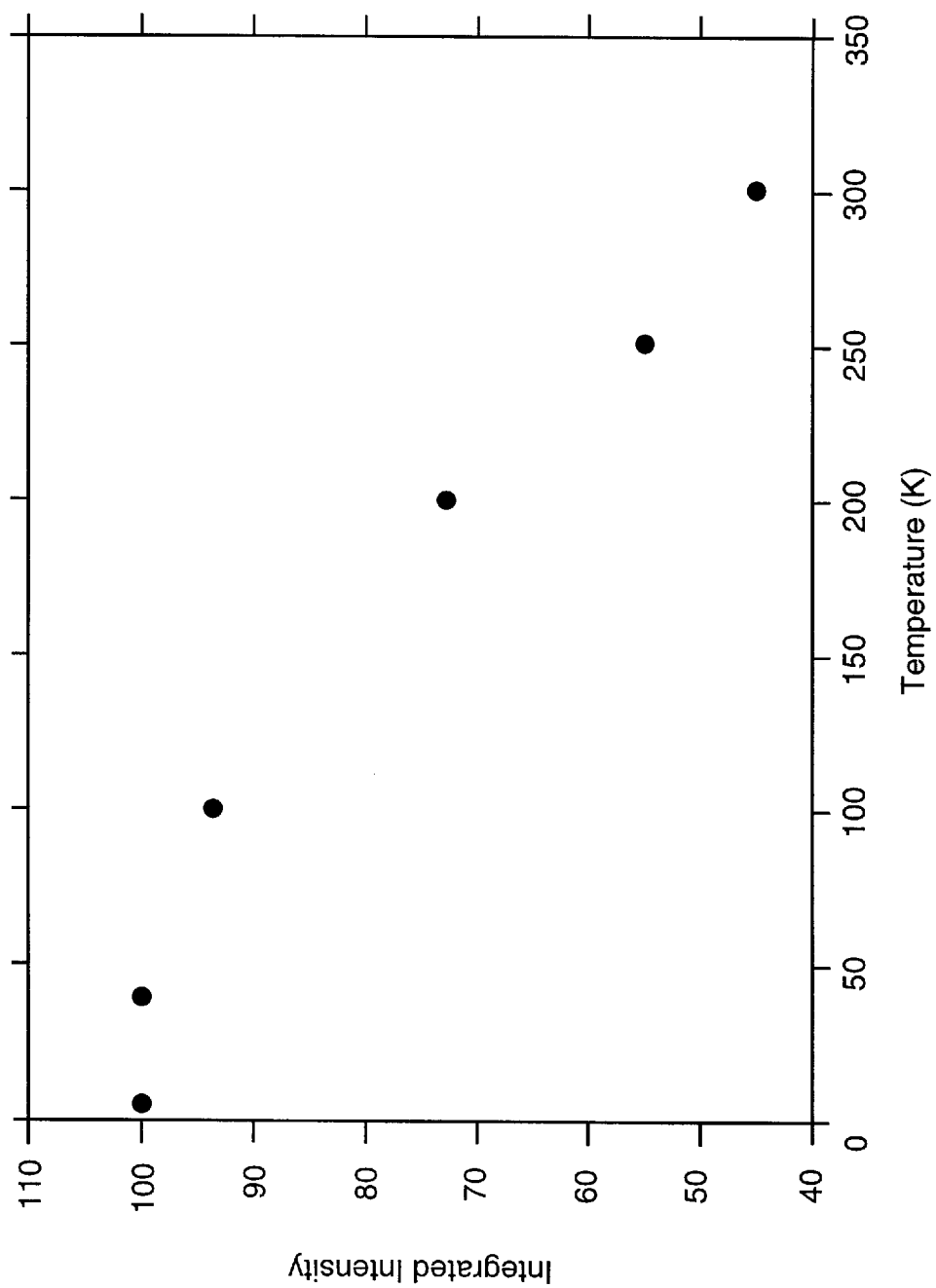
FIG. 2 is a temperature dependence for an integrated emission intensity.

A temperature dependence for an integrated emission intensity is illustrated in FIG. 2. As illustrated, the integrated emission intensity is nearly constant until about T=50 K. At temperatures beyond about T=50 K, non-radiative transitions within the $[FeO_4]^{5-}$ complex decrease. This decreases the luminescence efficiency. However at room temperature, the emission intensity retains a sufficiently strong intensity, so that the luminescence from the Feldspar particles can be readily detected.

The quartz sand raw material can be purified by detection and/or removal of impurities, such as Feldspar particles. Also, the quality of the quartz sand raw material can be assessed prior to use by detecting and quantifying an amount of Feldspar contained in a representative sample of quartz. This can be done by determining the percent of the entire lot that is undergoing detection and extrapolating appropriately.

Figure 3:
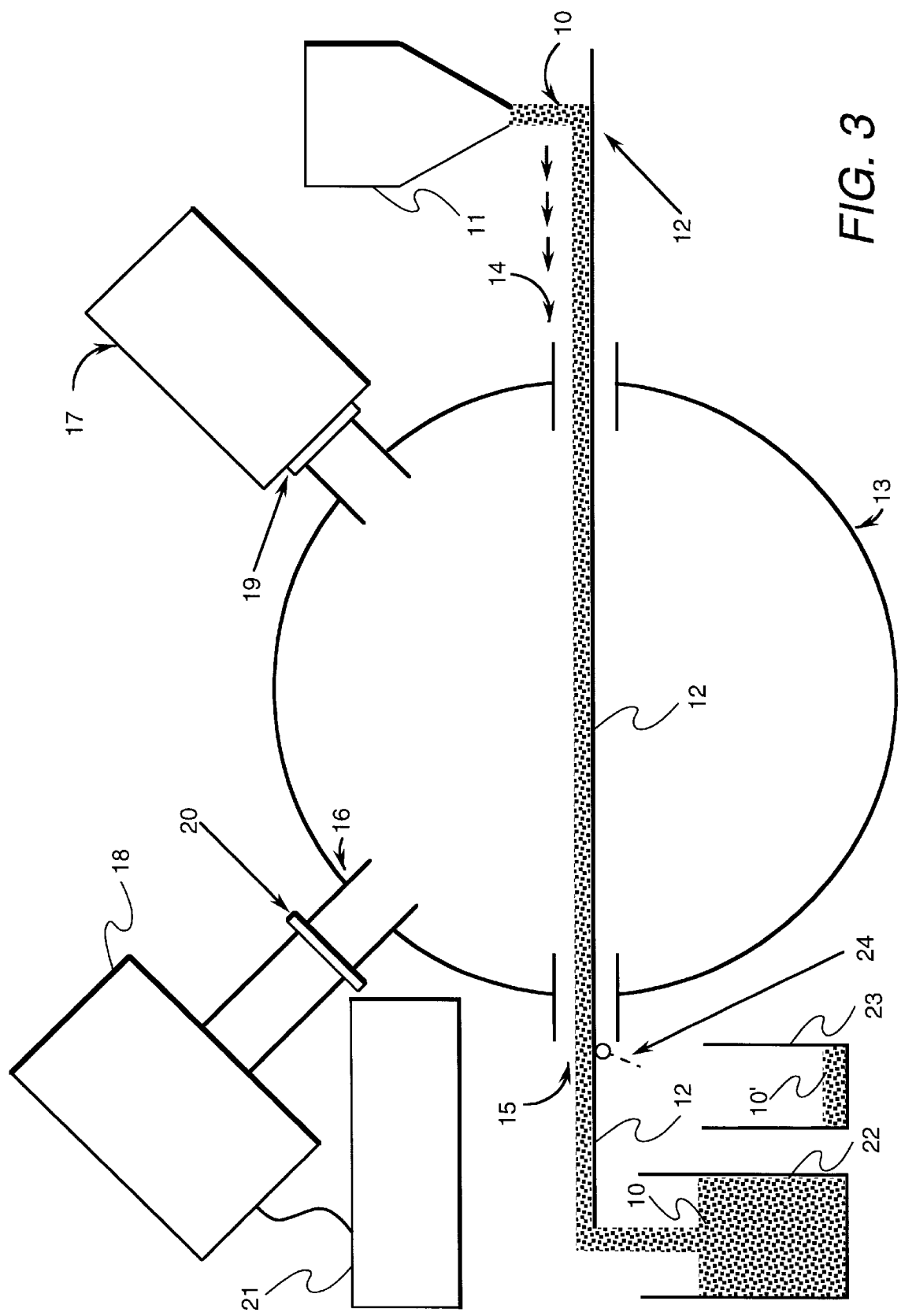
FIG. 3 is a schematic illustration of a first preferred embodiment of an apparatus for the evaluation of quartz sand in accordance with the invention.

The detection of the Feldspar impurity is accomplished by exciting the Feldspar luminescence using an appropriate energy source. FIG. 3 illustrates a schematic illustration of a first preferred embodiment of an apparatus for detecting impurities in quartz sand.

In FIG. 3, quartz sand 10 as a raw material is stored in a source 11. The source 11 may be a hopper, bin, storage silo or other similar storing means. The quartz sand is fed out of the hopper in a controlled manner by an appropriate feeding device (not illustrated). The feeding device can take any appropriate form, including but not limited to, by gravity and/or a gate; a screw conveyor, with or without a gate; a conveyor, auger or similar feeding device.

The quartz sand 10 is fed by the feeding device onto a conveyor 12. The quartz sand 10 is fed as a thin layer, preferably several grains thick. The conveyor 12 transports the quartz sand 10 in a path through an enclosure 13, where the quartz sand will be analyzed, and impurities detected. The conveyor 12 may take any appropriate form, including but not limited to a vibrating conveyor, a belt conveyor or other similar conveying system.

The enclosure 13 comprises an entrance 14 and an exit 15 for the conveyor 12. The enclosure 13 includes mounting structures 16 for mounting a light source and light detector assembly (to be described in detail hereinafter). The enclosure 13 provides a substantially ambient light free environment that prevents erroneous and undesirable light from being illuminated onto the quartz sand 10 and/or detected by the light detector assembly.

The enclosure 13 includes at least a light source 17 and at least one light detector assembly 18 mounted on the mounting structure 16. The mounting structure additionally includes structure for mounting at least one filter for each light source 17 and light detector assembly 18. For example, an excitation filter 19 is mounted with the light source 17, and an emission filter 20 is mounted with the light detector assembly 18. Although only one filter is illustrated for each light source 17 and light detector assembly 18, any number of filters of any type can be used dependent on the surrounding light and/or other conditions.

The light source 17 can take any appropriate form, dependent on the type of impurity to be detected. For Feldspar, it has been determined that an appropriate light source is a UV irradiation energy source or UV lamp. For Feldspar, the UV irradiation energy source is illuminated onto the quartz sand raw material. This excites the Feldspar impurity in the quartz sand 10 raw material, as discussed above with respect to the strong broad excitation band with a maximum at about approximately 260 nm in the Feldspar excitation spectrum, which is assigned to an $O^{2-} \rightarrow Fe^{3+}$ charge transfer transition.

The light from the light source 17 can be focused on the quartz sand 10 raw material at a region or volume of interest. Further, the light from the light source 17 can be focused on a larger area, using the enclosure 13 or other UV compatible optics.

The luminescence light, which is emitted from the excitation of the Feldspar impurity in the quartz sand 10, is collected by the light detector assembly 18. The light is first filtered, by an appropriate filter 20 or filters to reduce background luminescence. For example, background luminescence can originate from the quartz particles, ambient light, and/or other impurities.

The luminescence emission corresponding to and originating from the Feldspar is then detected with the light detector assembly 18. The light sensitive detector assembly 18 can take any appropriate form dependent on the wavelength of detected light. For example, the light detector assembly 18 can be but not limited to, a photomultiplier tube (PMT), a CCD camera, or a CID camera.

A signal is generated from the light detector 18, corresponding to a Feldspar impurity or impurities in the quartz sand 10. The magnitude of the signal from the light detector assembly 18 will be approximately generally proportionate to the concentration of Feldspar particles in the quartz sand 10 raw material and the volume being excited. For example, if the light detector assembly 18 is a single element detector, the signal is integrated from the entire illuminated volume. As a single element detector, the light detector assembly 18 generates a signal, and when the signal peaks may be indicative of at least one impurity particle in the illuminated volume.

Further, if desired, a signal processor 21 or controller receives the signal indicative of the impurity level in the quartz sand 10 from the light detector assembly 18. The signal processor 21 can then determine a quantitative level of impurities. If the signal processor 21 determines that the illuminated volume of quartz sand 10 has an impurity level within acceptable tolerances, the signal processor 21 permits the quartz sand 10 to pass to a collector 22, where quartz sand 10 with no impurities, or acceptably low impurity levels, are stored.

However, if the signal processor 21 determines that the illuminated volume of quartz sand 10 has an impurity level not within acceptable tolerances, the signal processor 21 directs high impurity quartz sand 10' to an impurity quartz sand collector 23, where the quartz sand 10' with non-acceptable or high impurity levels are stored.

The signal processor 21 acts to direct the high impurity quartz sand 10' to the impurity quartz sand collector 23, for example by diverting the high impurity quartz sand 10'. The high impurity quartz sand 10' can be diverted by a trap door 23, as illustrated in FIG. 3. However, this is merely exemplary, and any other appropriate diverter can be used, such as but not limited to a vacuum, gate, scoop, alternate conveyor or other means to divert high impurity quartz sand 10'.

The excitation light from the light source 17 can be of any appropriate wavelength, as long as it excites an impurity luminescence, such as a Feldspar luminescence. As illustrated in FIG. 1, a longer wavelength for the excitation light source, for example such, as about 200 nm to 260 nm, is preferred since this wavelength is less absorbed in the quartz sand 10 particles. An excitation light source, such as a mercury lamp, which has a strong line at 254 nm, is acceptable. This excitation light can be filtered to block any emission which is not useful in exciting the luminescence from the Feldspar. Of course, other light sources are within the scope of the invention.

A larger volume of raw quartz sand material can be sampled and the impurity level determined by a similar apparatus, as that described above. The sampling and detecting of a larger volume of quartz sand 10 can be accomplished by vibrating, or otherwise transporting, a stream of raw quartz sand particles under the light source 17, by a transporting device such as a conveyor. Preferably, the stream of quartz sand 10 is in a thin layer. The detecting of impurities, such as Feldspar particles, as they pass through the illuminated volume is accomplished substantially as discussed above.

For quartz sand 10 with sufficiently low concentrations of an impurity, such as Feldspar, and illuminated volumes that are sufficiently small enough, only one Feldspar particle will be illuminated at any given time. In this case, the light detector assembly 18 will register an increased signal level for the time that the Feldspar particle is illuminated. This increased signal can then be used to increment a counter (not illustrated), which may or may not be incorporated into the signal processor 21. The counter can then determine a total number of Feldspar particles in the quartz sand 10 for the illuminated volume.

Where the impurity concentration is too high, or the illuminated volume too great, it will be difficult to obtain a single increased signal for each impurity to effectively detect individual impurity particles in the quartz sand 10. There will simply be too many impurities in the quartz sand 10 to effectively determine individual impurity particles. In this situation, a signal from the light detector assembly 18 is integrated over time by the signal processor 21. The time integrated signal is used for an overall assessment of the impurity contamination in the quartz sand 10.

Further, if the Feldspar impurity concentration in the quartz sand is at a critical level and the light detector assembly 18 generates a signal indicating a critical level, where the critical level is defined as too many impurities in the quartz sand 10 for it to be useful for the intended purpose, the quartz sand 10 that is illuminated can be eliminated. The quartz sand 10 can be eliminated, as discussed above. Therefore, the Feldspar contamination in the quartz sand 10 used for a quartz melt can be kept below a critical level.

Another embodiment for detection, analysis and/or purification of impurity contamination in quartz sand will be discussed with reference to FIGS. 4–9. Generally speaking, in accordance with this embodiment, an image of UV illuminated quartz sand is transmitted onto an appropriate imaging device to determine impurities. For example, the imaging device can be a CCD or CID camera or other similar imaging device. The imaging of the UV illuminated quartz sand uses appropriate optics and filtration, such as those described above, for detection, analysis and/or purification of impurity contamination in quartz sand.

Figure 4:
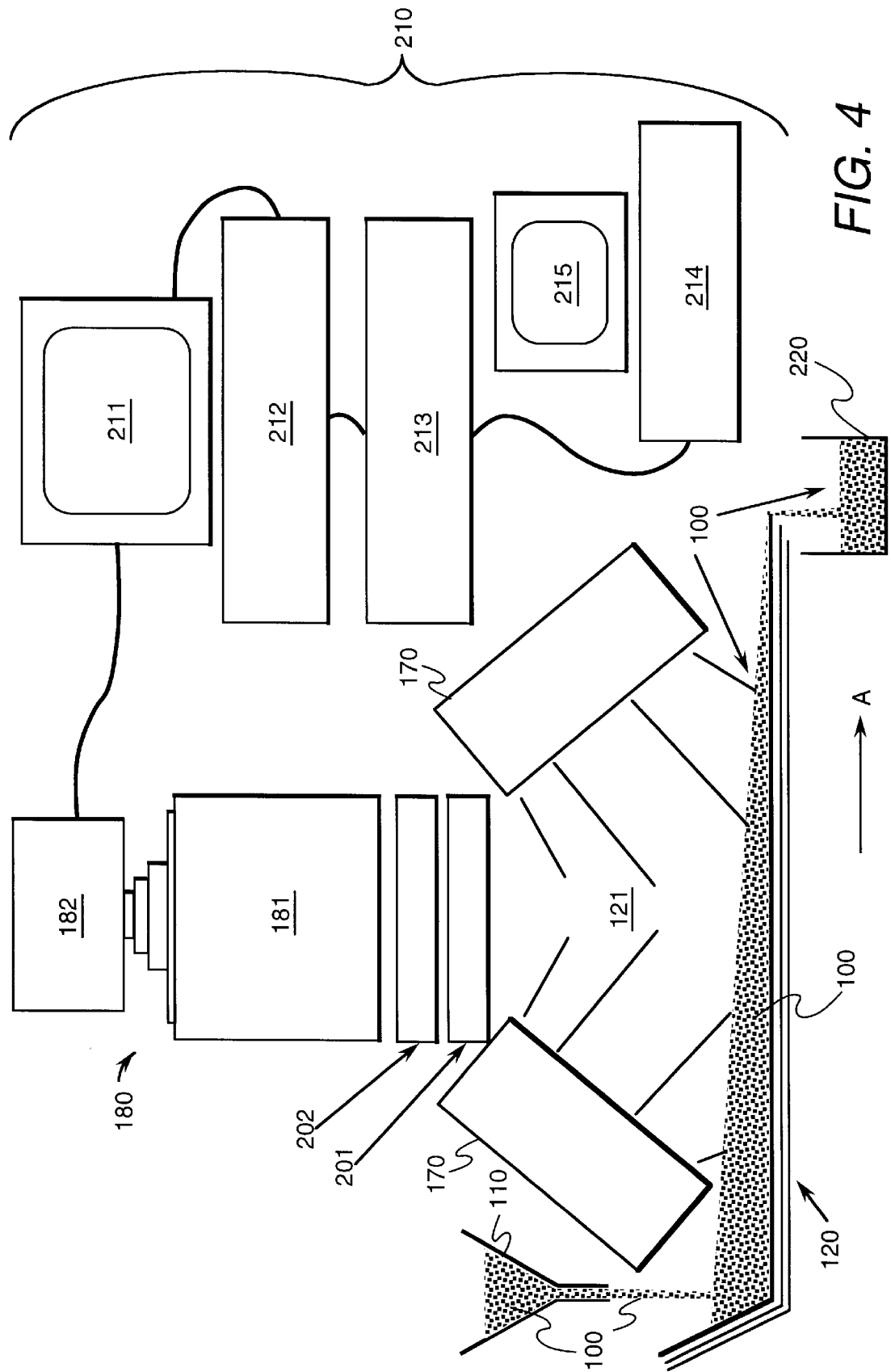
FIG. 4 is a schematic illustration of a second preferred embodiment of an apparatus for the evaluation of quartz sand in accordance with the invention.

FIG. 4 illustrates an impurity detection apparatus in accordance with the second preferred embodiment of the invention. In FIG. 4, quartz sand 100 as a raw material is stored in a source 110. The source 110 may be a hopper, bin, storage silo or other similar storing means. The quartz sand 100 is fed out of the source 110 in a controlled manner by an appropriate feeding device (not illustrated). The feeding device can take any appropriate form, including but not limited to, by gravity and/or a gate; a screw conveyor, with or without a gate, a conveyor, auger or similar feeding device.

The quartz sand 100 is fed by the feeding device onto a vibrating conveyor 120. The quartz sand 100 can be fed onto the vibrating conveyor 120 as a thin layer, preferably several grains thick. Alternatively, the vibrating conveyor 120 vibrates the quartz sand 100 to cause the quartz sand 100 to form a thin layer as it is transported. The vibrating conveyor 120 may take any appropriate form, including but not limited to a belt conveyor, vibrating chute conveyor or other similar vibrating conveyor.

The vibrating conveyor 120 transports the quartz sand 100 in a path so as to an area 121 where the quartz sand 100 will be analyzed, and any impurities detected. Mounted over the area 121 is at least one light source and at least one detector assembly (to be described in detail hereinafter).

The at least one light source 170, in the second preferred embodiment, comprises two light sources 170. The two light sources 170 are preferably UV light sources, as in the first preferred embodiment. Also, at least one light detector assembly 180 is mounted over the area 121.

As in the description of the first preferred embodiment, filters may be associated with the light source 170 and/or the light detector assembly 180. In FIG. 4, two separate filters, for example, emission filters 201 and 202 are mounted with the light detector assembly 180. Although only two filters are illustrated, any number of filters can be used dependent on the surrounding light and/or other conditions.

The light source 170 can take any appropriate form, for example UV light sources, dependent on the type of impurity to be detected, as discussed above. The light from light sources 170 illuminates on the quartz sand 100 raw material at a region or volume of interest in the area 121. Further, the light from light sources 170 can be focused on a larger or smaller area, such as using UV compatible optics.

The luminescence light, which is emitted from the excitation of the Feldspar impurity in the quartz sand 100, is collected by the light detector assembly 180. The light is first filtered, by filters 201 and 202, such as but not limited to, emission filters, to reduce background signal(s). For example, a background signal can originate from the quartz particles, ambient or background light, and/or other impurity luminescence.

The luminescence emission corresponding to and originating from the Feldspar is then detected with the light detector assembly 180. The light detector assembly in FIG.

4 comprises a lens 181 and a camera 182. The lens 181 and camera 182 can take any appropriate form, as long as they are able to sense and detect luminescence from an impurity.

A signal can be generated from the light detector assembly 180, corresponding to the Feldspar impurity or impurities in the quartz sand 100. The signal is then fed to a signal processor 210 or controller, which receives the signal indicative of the impurity level in the quartz sand 100 from the light detector assembly 180. The signal processor 210 can then determine a quantitative level of the impurity.

Furthermore, if desired, the signal processor 210 can determine that the illuminated volume of quartz sand 100 has an impurity level within acceptable tolerances, the signal processor 210 permits the quartz sand 100 to pass to a collector 220, where quartz sand 100 with no impurities or acceptably low impurity levels is stored for use.

However, if the signal processor 210 determines that the illuminated volume of quartz sand 100 has an impurity level not within acceptable tolerances, the signal processor 210 directs the quartz sand 100 to an impurity quartz sand collector (not illustrated), where quartz sand with unacceptably low impurity levels are stored so as not to be used. Alternatively, a counter can be incremented to quantify impurity content.

The signal processor 210 in FIG. 4 comprises a video monitor 211, a video signal amplifier 212, a video signal electronic filter 213 and a processor with an image analysis system 214 and monitor 215. The signal processor 210, in the second preferred embodiment as well as the first preferred embodiment, can take any form, as long as it can implement the description of the operation as disclosed herein.

The operation of the embodiment of FIG. 4 will now be described with reference to FIGS. 4–9. The quartz sand 100 is fed from the storage device 110 and fed onto the vibrating conveyor 120. The quartz sand 100 is transported under the area 121 where it is illuminated by the light sources 170 to excite luminescence in any impurities in the quartz sand 100, for example Feldspar particles.

After any Feldspar or impurity luminescence is detected by the light detector assembly 180, other light is reduced by the filters 201 and 202. The camera 182 then images the impurities and feeds the images to the signal processor 210 for detecting and determining if any impurities exist in the quartz sand 100 in the area 121.

Figure 5:
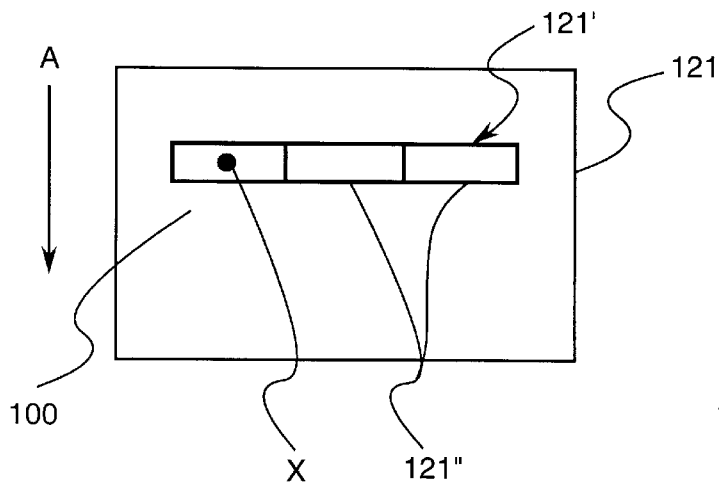
FIG. 5 is a top perspective camera image view of an area upon which a light source illuminates with computer generated regions of interest superimposed.

As illustrated in FIG. 5, a region of interest 121' is defined preferably as a small part of the area 121. The region of interest 121' is preferably a very small part of the image in the direction of movement Arrow A in FIG. 4, so that only a portion of the quartz sand 100 is evaluated for impurities (as discussed hereinafter). The area 121 can have any appropriate size as long as the signal processor 210 can evaluate signals, in accordance with the invention. The size of the region of interest 121' can vary dependent on the speed of the conveyor 120 (as in the first preferred embodiment the conveyor 12) and/or the speed of the signal processor 210 (or 21). Further, the region of interest can be subdivided into further smaller regions of interest 121" for further detailed analysis.

Figure 6:
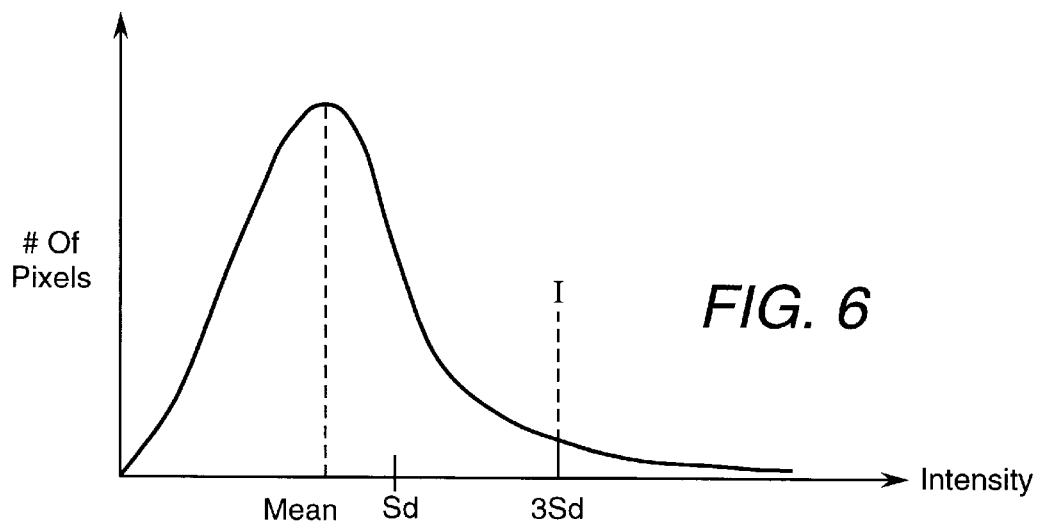
FIG. 6 is a histogram of the number of pixels versus intensity.

Once the region of interest 121' is illuminated and any impurities therein detected, a signal, for example a digitized signal, is generated by the camera 182 for the region of interest 121'. The signal is a pixel that represents a signal fluctuation, i.e. an impurity, illustrated as X in FIG. 5. The signal for the region of interest 121' is transmitted to signal processor 210, where a histogram is generated for the detected signals. FIG. 6 is representative of a histogram for a region of interest 121'.

The histogram of FIG. 6 illustrates the number of pixels on the vertical versus intensity or brightness of the pixels. A mean is determined for the histogram and a standard deviation is also determined, by any method known by those skilled in the art. Once the mean and standard deviation are known, an intensity point I is determined, so that any intensity greater than intensity point I could be an impurity. For example, if the intensity point I is determined to be three standard deviations greater than the mean, anything outside of that intensity point I could be an impurity particle or noise and should not be background signal(s).

The signal processor 210 converts all of the pixels in the region of interest 121'. The signal processor 210 sets a value for all pixels dependent on their value with respect to I. For example, for all pixels with an intensity less than I, a logical value of 0 is set and for all pixels with an intensity greater than or equal to I, a logical value of 1 is set. However, these logical values are merely exemplary, and any logical value could be used within the scope of the invention.

The above process is conducted for all regions of interest 121' in the area 121. Even more preferably, the above process is conducted for all smaller divisions 121" in the regions of interest 121' in the area 121. It has been determined that the smaller the region of interest, the better the detection results.

Next a spatial average for adjacent pixels is determined by the signal processor 210. Some exemplary adjacent pixel arrangements of data are illustrated in FIG. 7A–7C. The average is determined by processing the converted value for the pixels in a 3×3 matrix. The signal processor 210 then averages the matrices by adding the values for all of the nine values in the matrix together, and assigning this sum total as a spatial average. For example, with the kernel of FIG. 7A, a spatial average would be 3. For the arrangements of FIGS. 7B and 7C, the spatial average would be 5 and 7, respectively.

The signal processor 210 then determines that any spatial average with a value greater or equal to than a predetermined value, for example greater than or equal to Y=5, 6, 7, 8 or 9, is clearly representative of a particle, and does not represent noise. This representation of a particle is determined because the likelihood of a concentrated noise, after the above image processing, with a spatial average having the predetermined value is highly unlikely.

Figure 8:
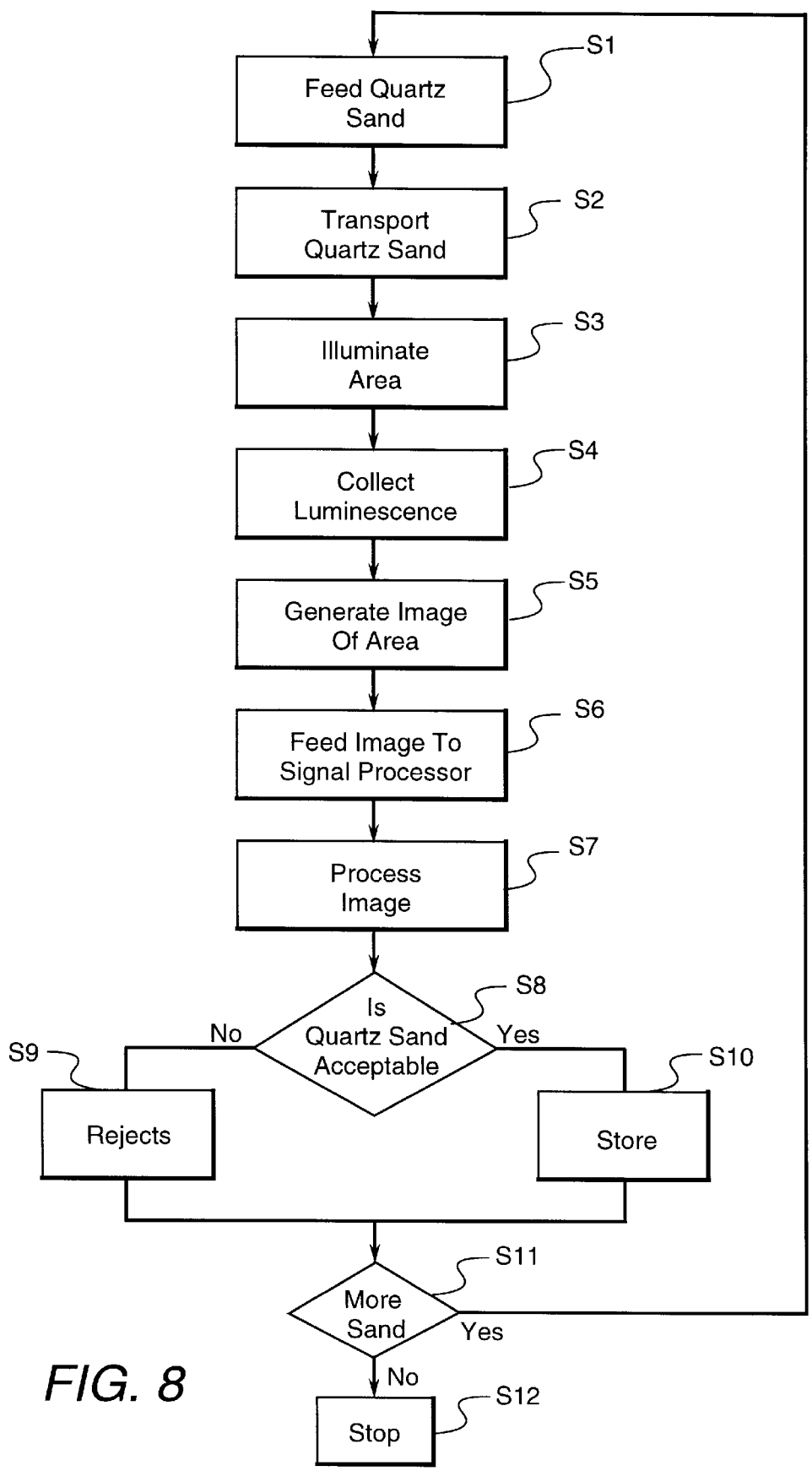
FIG. 8 is a flow chart of the process in accordance with the second preferred embodiment of the invention.

FIG. 8 illustrates a flow chart for the process in accordance with the second preferred embodiment of the invention. In step S1, the quartz sand 100 is fed by the feeding device onto a vibrating conveyor 120 as a thin layer, preferably several grains thick.

In step S2, the vibrating conveyor 120 transports the quartz sand 100 in a path so as to an area 121 where the quartz sand 100 will be analyzed, and any impurities detected.

In step S3, light from the light source 170 is focused on the quartz sand 100 raw material at a region or volume of interest in the area 121. In step S4, the luminescence light, which is emitted from the excitation of the impurity in the quartz sand 100, is collected by the light detector assembly 180.

In step S5, a signal is generated corresponding to the Feldspar impurity or impurities in the quartz sand 100. In step S6, the signal is fed to the signal processor 210, which receives the signal indicative of the impurity level in the quartz sand 100 from the light detector assembly 180.

In step S7, the signal processor 210 then determines an impurity level. In step S8, the signal processor 210 determines, based on the impurity level, if the illuminated volume of quartz sand 100 is acceptable, i.e., it has an impurity level within acceptable tolerances, the signal processor 210 permits the quartz sand 100 to pass to a collector 220, where quartz sand 100 with no or acceptably low impurity levels is stored in step S10. If step S8 is no, the impurity level is too high, the quartz sand 100 is rejected and not accepted in step S9.

After each of steps S9 and S10, the process determines if more sand is to be evaluated, in step S11. If there is more sand, the process repeats steps S1–S11, until there is no more sand. When there is no more sand to be evaluated, the process stops, in step S12.

Step S7 will now be described in more detail with reference to FIG. 9. In step S71, the camera 182 images the impurities. In step S72, the images are fed to the processor 210, with the image analysis system 214, for digitizing and detecting and determining if any impurities exist in the quartz sand 100 in the area 121. The digitizing can be performed at any point in the transfer of the images to the processor 210. The signal processor 210 generates a histogram for detected digitized signals or pixels in the region of interest 121".

In step S73, a mean and standard deviation are determined for the histogram. In step S74, a value for I is determined by the signal processor 210 for converting the signals for all pixels. Step S75, the signal processor 210 sets a value for all pixels dependent on their value with respect to the predetermined value I.

In step S76, a logic value, for example 0, is set for all pixels with an intensity less than I. If the value of I is equal to or greater than I, step S77 sets another logic value, for example 1. However, these values are merely exemplary and any logic value could be used.

Next in step S77, a spatial average for adjacent pixels is determined by the signal processor 210, by adding the values for all nine values in a formed 3×3 matrix of adjacent pixels, and assigning this sum total as a spatial average.

In step S78, the signal processor 210 determines if the spatial average has a value greater or equal to than a predetermined value Y, for example greater than or equal to Y=5, 6, 7, 8 or 9. If the spatial average is greater than or equal to the predetermined value Y, the signal processor 210 determines that this is representative of a particle, and does not represent noise. If the spatial average is less than the predetermined value Y, the signal processor 210 determines this is not an impurity, and that it represents noise. Then, at step S79, the process returns to step S8, in the flowchart of FIG. 8.

In the imaging as described above, the Feldspar impurity particles will appear as one or more connected pixels. These connected pixels, which are representative of the impurities, have a higher brightness compared to those pixels that actually image the quartz particles. The image with the one or more pixels can then be analyzed, as above, to identify, and if desirable, count Feldspar impurity particles in the area.

In a moving stream of quartz sand, the image analysis can be augmented to count only particles moving in a proper predetermined direction, for example the direction of movement A of the quartz sand imparted by a conveyor with a proper predetermined velocity. For Feldspar concentrations that are too high to identify individual particles, integrated counts over the total image can be used to evaluate the sand purity.

Further, the efficiency of the quartz sand illumination and luminescence light collection can be improved by mixing the quartz sand with a liquid. The liquid should preferably have an index of refraction that approximately matches the quartz sand's index of refraction. This minimizes any losses due to scattering. One possible liquid for quartz sand would be $CCl_4$, however this is merely exemplary and is not meant to limit the invention in any way.

Further, it is possible to cool the quartz sand prior to the quartz sand entering the detection apparatus. This cooling reduces thermal quenching of the quartz sand. Further, the cooling also increases the signal to noise in the detector.

Figure 10:
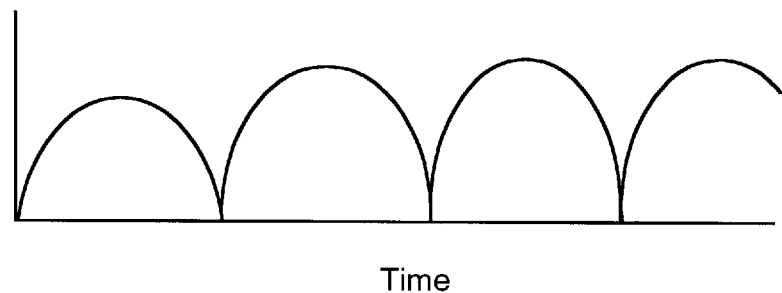
FIGS. 10 and 11 are phase diagrams representing the UV light from light sources.
Figure 11:
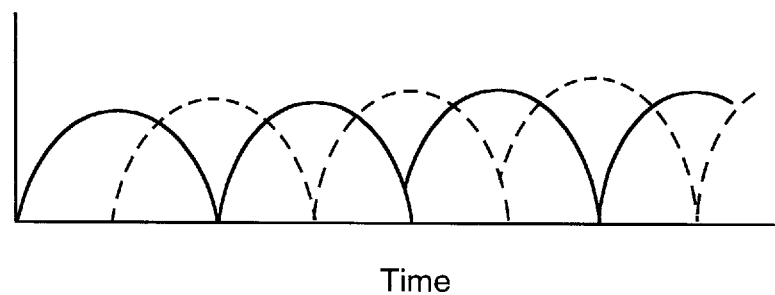

The light from an AC powered light source, i.e., a low pressure Hg light source is emitted in cycles over time, as illustrated in FIG. 10. Thus, there are "peaks" and "valleys" in the light, where the signal in the valleys may not be clearly detectable. It has been determined that the provision of another AC powered light source will alleviate many of the clarity issues, where the another AC powered light source is 90° out of phase from the first AC powered light source as illustrated in FIG. 11. Further, the number of light sources can be increased with predetermined phases so as to provide an essentially constant light source.

Throughout this description of the invention, Feldspar has been used as an example of the impurity. However, as discussed above, the detection of impurities using luminescence can be extended to any luminescent mineral other than the bulk material. Further, although the specific example of $Fe^{3+}$ luminescence in Feldspar has been used as an example, it is also possible to extend this to any other impurity, which has a luminescence at wavelengths sufficiently different from the excitation wavelength. Thus, the emission can be detected using the techniques described above.

While the embodiments described herein are preferred, it will be appreciated from the specification that various disclosed combinations of elements, variations or improvements therein may be made by those skilled in the are that are within the scope of the invention.

What is claimed is:

1. An apparatus for detection of impurities in quartz sand, the apparatus comprising:
   at least one light source, wherein the at least one light source comprises a UV irradiation energy source;
   at least one light detector assembly;
   a transport device that moves quartz sand to be illuminated by the at least one light source, the at least one light source illuminates the quartz sand to excite luminescence emission from impurities, the at least one light detector assembly receiving luminescence emission from the impurity and generating at least one signal indicative of the excited luminescence emission from the impurity;
   a signal processor that receives the at least one signal from the at least one light detector assembly, the signal processor comprises at least a video monitor, a video signal amplifier, a video signal electronic filter, and a processor with an image analysis system;
   wherein the signal processor determines if the at least one signal represents an impurity in quartz sand.

2. The apparatus according to claim 1, wherein the transport device comprises a storage device for quartz sand.

3. The apparatus according to claim 1, wherein the transport device comprises a conveyor.

4. An apparatus according to claim 3, wherein the conveyor is a vibrating conveyor.

5. An apparatus according to claim 1, wherein the transporting device forms a thin layer of quartz sand.

6. An apparatus according to claim 1, wherein the transport device is a vibrating conveyor, and the vibrating conveyor forms a thin layer of quartz sand.

7. An apparatus according to claim 1, further comprising an enclosure providing an essentially ambient light-free enclosure, the enclosure mounting the at least one light source and at least one light detector assembly.

8. An apparatus according to claim 7, wherein the enclosure includes an entrance and exit for the transporting device to move the quartz sand to and from an area to be illuminated.

9. An apparatus according to claim 1, wherein the at least one light source comprises a plurality of light sources.

10. An apparatus according to claim 1, wherein the at least one light source further comprises at least one excitation filter.

11. An apparatus according to claim 1, wherein the at least one light detector assembly comprises at least one emission filter that reduces background signal.

12. An apparatus according to claim 11, wherein the at least one emission filter comprises a plurality of emission filters.

13. An apparatus according to claim 1, the signal processor comprises a counter, wherein the counter is incremented to quantify impurity content of the quartz sand.

14. An apparatus according to claim 1, wherein the at least one light detector generates a signal, and the light detector generates an increased signal representative of an excited luminescence emission.

15. An apparatus according to claim 14, wherein the signal is transmitted to the signal processor to determine if the signal is representative of an impurity.

16. An apparatus according to claim 1, wherein if the signal processor determines if the signal represents an impurity, the signal processor diverts the quartz sand.

17. An apparatus according to claim 16, wherein the transport device further comprises a diverter selected from the group consisting of a trap door, a vacuum, a gate, a scoop, and an alternate conveyor and the signal processor activates the diverter to divert quartz sand.

18. An apparatus according to claim 1, the signal processor directs the transport device to move the quartz sand to an acceptable quartz sand storage bin if the signal processor determines that the at least one signal from the at least one light detector assembly is not indicative of an impurity.

19. An apparatus according to claim 1, the at least one light detector assembly further comprises a lens and camera assembly, wherein the lens and camera assembly generates an image of the quartz sand that has been illuminated by the at least one light source.

20. An apparatus according to claim 1, wherein the signal processor digitizes a video image;
generates a region of interest;
generates a histogram for signal in the image;
determines a mean and standard deviation for the histogram;
sets a value for the signals dependent on a predetermined intensity point;
sets a first logical value for the signals with an intensity less than the predetermined value and a second logical value for the signals with a value greater than or equal to the predetermined intensity point;
determines an average for all adjacent signals;
compares the average with a predetermined value, wherein an average being equal to or greater than the predetermined value is indicative of an impurity.

21. A method for detecting impurities in quartz sand using an apparatus comprising at least one light source; at least one light detector assembly; a transport device; and a signal processor that receives the at least one signal from the at least one light detector assembly; the method comprising:
moving quartz sand by the transport device;
illuminating the quartz sand by the at least one light source to excite luminescence emission from impurities in the quartz sand, the illuminating comprising illuminating the quartz sand by a UV irradiation energy source;
receiving luminescence emission from the impurity by the at least one light detector;
generating at least one signal indicative of the excited luminescence emission from the impurity;
receiving the at least one signal from the at least one light detector assembly in the signal processor,
determining if the at least one signal represents an impurity in quartz sand, wherein the determining if the at least one signal represents an impurity in quartz sand comprising:
digitizing a video image;
generating a region of interest;
generating a histogram for signals from the image at the region of interest;
determining a mean and standard deviation for the histogram;
setting a value for signals dependent on a predetermined intensity point;
setting a first logical value for signals with an intensity less than the predetermined value and a second logical value for signals with a value greater than or equal to the predetermined intensity point;
determining an average for all adjacent signals;
comparing the average with a predetermined value, wherein the average being equal to or greater than the predetermined value is indicative of an impurity.

22. A method according to claim 21, further comprising discharging the quartz sand onto the transport device from a storage device.

23. A method according to claim 21, wherein the transport device comprises at least one of a belt conveyor and a vibrating conveyor.

24. A apparatus according to claim 21, further comprising forming a thin layer of quartz sand by the transporting device.

25. A method according to claim 21, further comprising blocking outside light.

26. A method according to claim 21, further comprising illuminating the quartz sand by a plurality of light sources.

27. A method according to claim 21, further comprising filtering the light from the at least one light source further by at least one excitation filter.

28. A method according to claim 21, further comprising filtering the detected light by at least one emission filter to reduce background signals.

29. A method according to claim 21, further comprising generating an increased signal representative of an excited luminescence emission.

30. A method according to claim 29, further comprising transmitting the increased signal to the signal processor to determine if the signal is representative of luminescent emission from an impurity.

31. A method according to claim 21, further comprising diverting the quartz sand if the signal processor determines if the signal represents luminescent emission from an impurity.

32. A method according to claim 31, wherein diverting further comprises activating a diverter selected from the group consisting of a trap door, a vacuum, a gate, a scoop, and an alternate conveyor by the signal processor to divert quartz sand.

33. A method according to claim 21, wherein the at least one light detector assembly comprises a lens and camera assembly.

34. A method according to claim 21, further comprising;
  adding a liquid to increase efficiency and luminescence emission collection.

35. A method according to claim 21, further comprising;
  cooling to reduce thermal quenching in the quartz sand.

36. A method according to claim 21, further comprising;
  illuminating the quartz sand with a plurality of light sources, wherein phases of the plurality of light sources are out of phase, and a generally constant light source is provided.

* * * * *

UNITED STATES PATENT AND TRADEMARK OFFICE
CERTIFICATE OF CORRECTION

PATENT NO. : 5,818,577

DATED : October 6, 1998

INVENTOR(S) : Steven J. Duclos et al.

It is certified that error appears in the above-identified patent and that said Letters Patent is hereby corrected as shown below:

Drawings:
In Figure 1, in the "x" axis labeled "Wavelength (nm)", please change "250 305 300 360 200 200 200 200" to --250 275 300 360 470 580 690 800--.

Figure 9:
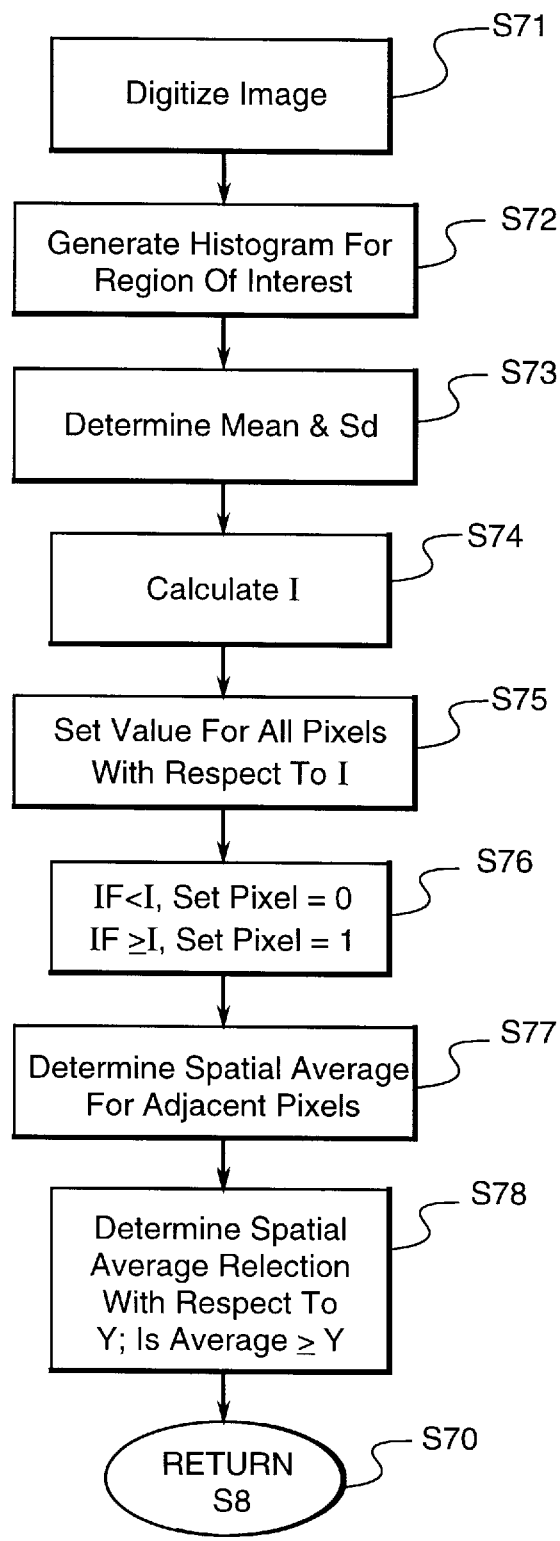
FIG. 9 is a flow chart further explaining the process of the second preferred embodiment.

In Figure 9, change "Relection" to --Relation--.

Column 2, line 10, change "$Fe^{3+}$" to --$Fe^{3+}$--.

Column 3, lines 4, 5 (two occurrences), 8, 13 and 21, change "$Fe^{3+}$" to --$Fe^{3+}$--.

Column 4, line 21, change "$Fe^{3+}$" to --$Fe^{3+}$--.

Signed and Sealed this

Ninth Day of February, 1999

Attest:

*Attesting Officer*

*Acting Commissioner of Patents and Trademarks*

UNITED STATES PATENT AND TRADEMARK OFFICE
CERTIFICATE OF CORRECTION

PATENT NO. : 5,818,577

DATED : October 6, 1998

INVENTOR(S) : Stephen J. Duclos et al.

It is certified that error appears in the above-identified patent and that said Letters Patent is hereby corrected as shown below:

On the title page, item [75]:
Tha name of Inventor Jacob Charles Borscheller should be correctly spelled as Jacob Charles Bortscheller.

Signed and Sealed this

Twenty-third Day of March, 1999

Attest:

Q. TODD DICKINSON

*Attesting Officer*  *Acting Commissioner of Patents and Trademarks*